United States Patent
Obaidat et al.

(10) Patent No.: US 10,490,323 B2
(45) Date of Patent: Nov. 26, 2019

(54) METHOD OF SYNTHESIZING MAGNETITE/MAGHEMITE CORE/SHELL NANOPARTICLES

(71) Applicant: UNITED ARAB EMIRATES UNIVERSITY, Al-Ain (AE)

(72) Inventors: Ihab M. Obaidat, Al Ain (AE); Chiranjib Nayek, Al Ain (AE)

(73) Assignee: United Arab Emirates University, Al-Ain (AE)

( * ) Notice: Subject to any disclaimer, the term of this patent is extended or adjusted under 35 U.S.C. 154(b) by 93 days.

(21) Appl. No.: 15/808,496

(22) Filed: Nov. 9, 2017

(65) Prior Publication Data
US 2019/0139685 A1    May 9, 2019

(51) Int. Cl.
*C01G 49/06* (2006.01)
*H01F 1/00* (2006.01)
(Continued)

(52) U.S. Cl.
CPC .......... *H01F 1/0054* (2013.01); *C01G 49/06* (2013.01); *C01G 49/08* (2013.01); *B82Y 5/00* (2013.01);
(Continued)

(58) Field of Classification Search
CPC ....... H01F 1/0054; C01G 49/08; C01G 49/06; Y10S 977/896; Y10S 977/811;
(Continued)

(56) References Cited

U.S. PATENT DOCUMENTS

2004/0219361 A1    11/2004    Cui et al.

FOREIGN PATENT DOCUMENTS

| CN | 103480308 A | 1/2014 |
|---|---|---|
| CN | 105769812 A | 7/2016 |

OTHER PUBLICATIONS

Frison, Ruggero, et al. "Magnetite-Maghemite Nanoparticles in the 5-15 nm Range: Correlating the Core-Shell Composition and the Surface Structure to the Magnetic Properties. A Total Scattering Study." Chemistry of Materials 25.23 (2013): 4820-4827.*

(Continued)

*Primary Examiner* — Richard M Rump
(74) *Attorney, Agent, or Firm* — Richard C. Litman; Nath, Goldberg & Meyer

(57) ABSTRACT

The method of synthesizing magnetite/maghemite core/shell nanoparticles is a modified co-precipitation method for producing iron oxide ($Fe_3O_4/\gamma$-$Fe_2O_3$) nanoparticles that allows for production of the $Fe_3O_4/\gamma$-$Fe_2O_3$ core/shell nanoparticles with a desired shell thickness ranging between about 1 nm to 5 nm for biomedical and data storage applications. Aqueous solutions of ferric and ferrous salts are mixed at room temperature and pH of the mixture is raised to 10. The mixture is then heated at 80° C. for different lengths of time at atmospheric pressure to adjust particle size, and the precipitate is dried at 120° C. in vacuum. Oxidation in an oxygen atmosphere for different lengths of time is used to adjust the thickness of the $\gamma$-$Fe_2O_3$ shell.

8 Claims, 5 Drawing Sheets

(51) Int. Cl.
    *C01G 49/08* (2006.01)
    *B82Y 5/00* (2011.01)
    *B82Y 25/00* (2011.01)
    *B82Y 10/00* (2011.01)
    *B82Y 40/00* (2011.01)

(52) U.S. Cl.
    CPC ............. *B82Y 10/00* (2013.01); *B82Y 25/00* (2013.01); *B82Y 40/00* (2013.01); *C01P 2004/04* (2013.01); *C01P 2004/64* (2013.01); *C01P 2004/84* (2013.01); *C01P 2006/42* (2013.01); *Y10S 977/773* (2013.01); *Y10S 977/811* (2013.01); *Y10S 977/892* (2013.01); *Y10S 977/896* (2013.01); *Y10S 977/904* (2013.01); *Y10S 977/943* (2013.01)

(58) Field of Classification Search
    CPC ............ Y10S 977/773; Y10S 977/904; Y10S 977/892; Y10S 977/943; B82Y 40/00; B82Y 10/00; B82Y 5/00; B82Y 25/00; C01P 2004/64; C01P 2004/84; C01P 2006/42

See application file for complete search history.

(56) References Cited

OTHER PUBLICATIONS

Santoyo Salazar, Jaime, et al. "Magnetic iron oxide nanoparticles in 10-40 nm range: composition in terms of magnetite/maghemite ratio and effect on the magnetic properties." Chemistry of materials 23.6 (2011): 1379-1386.*

Hwang, Yosun et al. "Exchange bias behavior of monodisperse Fe 3 O 4/γ-Fe 2 O 3 core/shell nanoparticles." Current Applied Physics 12.3 (2012): 808-811.

Lee, Shih-Chi et al. "Effects of core/shell structure on magnetic induction heating promotion in Fe3O4/γ-Fe2O3 magnetic nanoparticles for hyperthermia." Applied Physics Letters 103.16 (2013): 163104.

* cited by examiner

METHOD OF SYNTHESIZING MAGNETITE/MAGHEMITE CORE/SHELL NANOPARTICLES

BACKGROUND

1. Field

The disclosure of the present patent application relates to magnetic core/shell nanoparticles for biomedical, data storage, and other applications, and particularly to a method of synthesizing magnetite/maghemite core/shell nanoparticles that allows preparation of nanoparticles of similar core diameter and various thicknesses in order to tune the exchange bias and control coercivity and saturation magnetization.

2. Description of the Related Art

Some ferromagnetic nanoparticles exhibit a property known as exchange bias, which is a displacement of hysteresis loops along the magnetic field axis. Exchange bias was first found in fine cobalt particles, and subsequently attributed to an exchange interaction at the interface between a ferromagnetic (FM) cobalt core and an antiferromagnetic (AFM) CoO shell. Such exchange bias at the FM/AFM interface is expected to give rise to an enhanced coercivity. Despite the original discovery in cobalt particles, the exchange bias phenomenon has mostly been studied in thin film systems, simply because it is easier to prepare FM/AFM combinations in films with a greater control of the interface than has been practically possible with nanoparticles.

Magnetite ($Fe_3O_4$) and maghemite ($\gamma\text{-}Fe_2O_3$) are both ferrimagnetic materials. Recent advances made in the field of magnetic nanoparticle synthesis has prompted renewed interest in nanoparticles in general, and exchange bias systems in particular. Among iron-related systems, most of the recent work has been focused on exchange bias behavior in $\gamma\text{-}Fe_2O_3$, $\gamma\text{-}Fe_2O_3$ coated iron nanoparticles, and $Fe_3O_4$ core (ferri)-FeO shell (AFM) systems. Study of an exchange bias phenomenon in core/shell $Fe_3O_4/\gamma\text{-}Fe_2O_3$ nanoparticles, in which the surface of $Fe_3O_4$ nanoparticles has been naturally modified to a $\gamma\text{-}Fe_2O_3$ shell during the chemical synthetic process, is of particular interest, given that $Fe_3O_4/\gamma\text{-}Fe_2O_3$ nanoparticles have a wide range of uses, including medical applications, such as local magnetic hyperthermia and magnetic resonance imaging, and magnetic data storage. With regard to the former, $Fe_3O_4/\gamma\text{-}Fe_2O_3$ nanoparticles have unique biocompatibility with the human body, thus increasing interest in these particles. It is known that the magnetic properties of particles, particularly nanoparticles, are affected by the size and surface properties of the particles. It would be desirable to be able to easily produce such nanoparticles, particularly with easily tunable, or selective, shell thicknesses. Thus, a method of synthesizing magnetite/maghemite core/shell nanoparticles solving the aforementioned problems is desired.

SUMMARY

The method of synthesizing magnetite/maghemite core/shell nanoparticles is a modified co-precipitation method for producing iron oxide ($Fe_3O_4/\gamma\text{-}Fe_2O_3$) nanoparticles that allows for production of the $Fe_3O_4/\gamma\text{-}Fe_2O_3$ core/shell nanoparticles with a desired shell thickness ranging between about 1 nm to 5 nm for biomedical and data storage applications. Aqueous solutions of ferric and ferrous salts are mixed at room temperature and pH of the mixture is raised to 10. The mixture is then heated at 80° C. for different lengths of time at atmospheric pressure to adjust particle size, and the precipitate is dried at 120° C. in vacuum. Oxidation in an oxygen atmosphere for different lengths of time is used to adjust the thickness of the $\gamma\text{-}Fe_2O_3$ shell.

Using this method, it was possible to synthesize $Fe_3O_4/\gamma\text{-}Fe_2O_3$ core/shell nanoparticles of similar core diameter (8 nm) and various shell thickness (1 nm, 3 nm, and 5 nm). This produced a nonconventional exchange bias effect in the two samples with smaller shell thickness, which was absent with larger shell thickness. There was a critical temperature of 100K at which coercivity was minimum, and coercivity increased monotonically above 100K. Saturation magnetization enhanced drastically to 120 emu/g (50% larger than bulk value) at a shell thickness of 3 nm after field cooling. Thus, the method produces nanoparticles of great interest in biomedical applications that require magnetic nanoparticles that are easily synthesized, have high saturation magnetization, are biodegradable and stable at room temperature, and have magnetic properties that are tuneable by altering reaction conditions.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
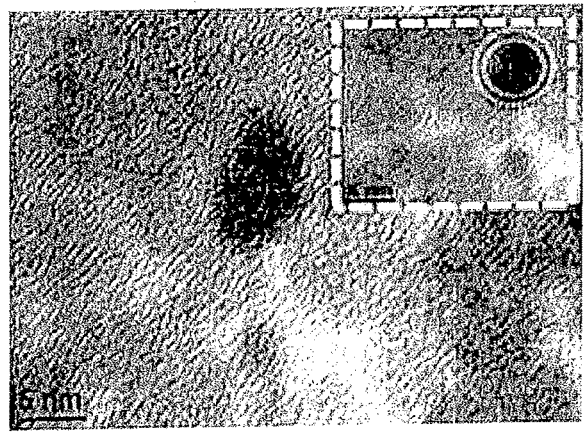
FIG. 1A is a transmission electron microscope (TEM) photomicrograph of a first sample (1 hr reaction time, 1 nm shell thickness) of $Fe_3O_4/\gamma\text{-}Fe_2O_3$ core/shell nanoparticles produced by the present method, with a high resolution TEM (HRTEM) image of the first sample shown in an inset.

The method of synthesizing magnetite/maghemite core/shell nanoparticles is a modified co-precipitation method for producing iron oxide ($Fe_3O_4/\gamma$-$Fe_2O_3$) nanoparticles that allows for production of the $Fe_3O_4/\gamma$-$Fe_2O_3$ core/shell nanoparticles with a desired shell thickness ranging between about 1 nm to 5 nm for biomedical and data storage applications. Aqueous solutions of ferric and ferrous salts are mixed at room temperature and pH of the mixture is raised to 10. The mixture is then heated at 80° C. for different lengths of time to adjust particle size, and the precipitate is dried at 120° C. in vacuum. The precipitate is then oxidized is oxygen atmosphere for different lengths of time to adjust thickness of the $\gamma$-$Fe_2O_3$ shell.

There are two main parameters in our synthesis method: (1) the reaction time, and (2) the diffusion time. The reaction time is the duration in which the mixed solution was allowed to react under particular conditions (such as temperature, pressure). The reaction time was varied to obtain different initial particle diameters. The atomic oxygen plays a major role inducing $\gamma$-$Fe_2O_3$ phase. This is due to the direct logarithmic kinetic diffusion with a logarithmic relation between $\gamma$-$Fe_2O_3$ thicknesses versus oxygen exposure time. The oxidation (diffusion) was allowed to occur in ambient atmosphere (in the presence of oxygen). In this way the reaction mechanism, which involves inward anionic diffusion, is responsible for the occurrence of $\gamma$-$Fe_2O_3$ phase at the core surface. The diffusion time was varied to obtain different $\gamma$-$Fe_2O_3$ shell thicknesses. By trial and error, we have optimized these two parameters to obtain fixed core and different shell thicknesses. The larger the reaction time, the larger is the initial particle size. The larger the oxidation (diffusion) time, the larger is the oxidized layer (shell thickness). Thus, to obtain larger/smaller shell thickness, we started with larger/smaller particles (longer/shorter reaction times) and allowed for longer/shorter diffusion times. By optimizing these two times we were able to determine the suitable initial particle size for each diffusion time such that we obtain fixed core for each case. We found that when the reaction time is 1 h and the diffusion time is 1 h the core diameter is 8 nm and the shell thickness is 1 nm. When the reaction time is 2 h and the diffusion time is 2 h, the core diameter is 8 nm and the shell thickness is 3 nm. When the reaction time is 3 h and the diffusion time is 3 h, the core diameter is 8 nm and the shell thickness is 5 nm.

In an exemplary procedure, $FeCl_3.6H_2O$ (0.1 M) and $FeCl_2.4H_2O$ (0.05 M) are used as precursor materials. Each precursor is dissolved in deionized water, separately, to form respective aqueous solutions thereof. The two aqueous solutions are mixed, at room temperature. Ammonium hydroxide solution (25%) is added in a dropwise manner to the mixture until it reaches a pH of 10. The mixture is then maintained at a temperature of 80° C. at atmospheric pressure for one hour, two hours, or three hours while the reaction occurs, resulting in a black precipitate. The selection of reaction time determines the size of the nanoparticles. Following the selected reaction time, the black precipitate is extracted and dried at a temperature of 120° C. in vacuum to yield the resultant nanoparticles. This procedure resulted in core/shell nanoparticles having a constant core diameter of 8 nm and a shell thickness of 1 nm (1 hr heating), 3 nm (2 hrs heating) or 5 nm (3 hrs heating).

It has been reported that a reaction mechanism involving inward anionic diffusion is responsible for the $\gamma$-$Fe_2O3$ phase. The atomic oxygen plays a major role inducing the $\gamma$-$Fe_2O_3$ phase. This is due to direct logarithmic kinetic diffusion with a logarithmic relation between $\gamma$-$Fe_2O_3$ thicknesses versus oxygen exposure time. Thus, instead of keeping the nanoparticles in vacuum, they were allowed to oxidize in ambient atmosphere for different time spans. The smaller particles are allowed to oxidize in an oxygen atmosphere for a shorter time and the largest particles are allowed to oxidize for a longer time to build thicker shells with the same core dimensions. The nanoparticles produced with a one hour reaction time in open air had the smallest $\gamma$-$Fe_2O_3$ shell thickness (1 nm), whereas nanoparticles produced with a three hour reaction time in open air had the largest $\gamma$-$Fe_2O_3$ shell thickness (5 nm). An X-ray diffraction characterization was performed to confirm the materials phase. Transmission electron microscopy (TEM) and high resolution transmission electron microscopy (HRTEM) were used to investigate the morphology of the nanoparticles. Selected area electron diffraction (SAED) and Mossbauer spectroscopy were conducted to confirm the phases of the core and shell materials.

Figure 1B:
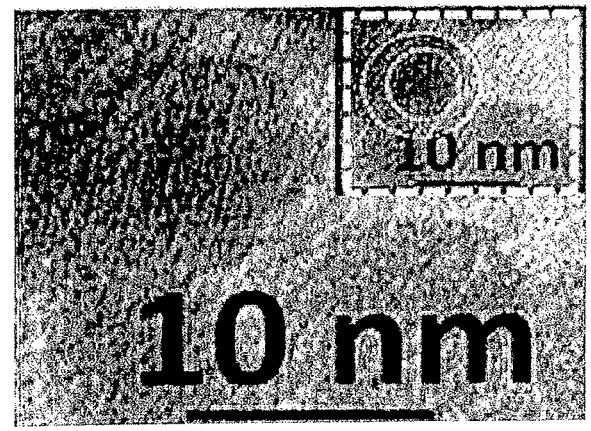
FIG. 1B is a TEM photomicrograph of a second sample (2 hr reaction time, 3 nm shell thickness) of $Fe_3O_4/\gamma\text{-}Fe_2O_3$ core/shell nanoparticles produced by the present method, with a HRTEM image of the second sample shown in an inset.
Figure 1C:
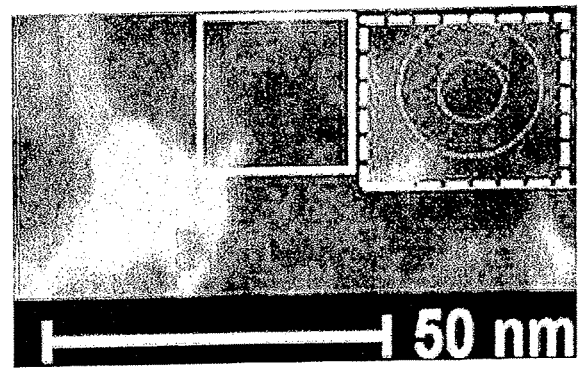
FIG. 1C is a TEM photomicrograph of a third sample (3 hr reaction time, 5 nm shell thickness) of $Fe_3O_4/\gamma\text{-}Fe_2O_3$ core/shell nanoparticles produced by the present method, with a HRTEM image of the third sample shown in an inset.

FIG. 1A is a transmission electron microscope (TEM) image of a first sample (sample S1) of iron oxide ($Fe_3O_4$/$\gamma$-$Fe_2O_3$) nanoparticles produced by the present method, with a high resolution transmission electron microscopy (HRTEM) image of sample S1 shown in an inset. Sample S1 was prepared with a one-hour reaction time. Similarly, FIG. 1B is a TEM image of a second sample (sample S1) of iron oxide ($Fe_3O_4$/$\gamma$-$Fe_2O_3$) nanoparticles produced by the present method, with a HRTEM image of sample S2 shown in an inset. Sample S2 was prepared with a two-hour reaction time. FIG. 1C is a TEM image of a third sample (sample S3) of iron oxide ($Fe_3O_4$/$\gamma$-$Fe_2O_3$) nanoparticles produced by the present method, with a HRTEM image of sample S3 shown in an inset. Sample S3 was prepared with a three-hour reaction time.

The conventional exchange bias effect is induced in a ferromagnetic material when structures with ferromagnetic (FM)/antiferromagnetic (AFM) interfaces are field-cooled (i.e., cooled under an applied magnetic field) from a temperature, T, where $T_N$<T ($T$>$T_C$) down to T<$T_N$. Here, $T_N$ is the Neel temperature (magnetic order temperature) of the AFM material and $T_C$ is the Curie temperature (magnetic order temperature). The exchange bias effect is associated with the exchange coupling at the interface between an AFM and an FM material. The exchange coupling can occur at the interface of any two materials with different spin structures when they are cooled down in the existence of a magnetic field. Thus, the exchange coupling induces a unidirectional exchange anisotropy which appears as a horizontal shift (along the applied magnetic field axis) in the center of the magnetic hysteresis loop. The direction of this shift is opposite to the sign of the cooling field. The two main features of the presence of an exchange bias in a layered and core/shell systems are (1) a shift of the center of field-cooled magnetic hysteresis loop in a direction opposite to the sign of the cooling field, and/or (2) an enhancement of the coercivity.

Sample S3 displayed a complete disappearance of the exchange bias effect at all field-cooled values and at all temperatures. An unconventional exchange bias in sample S1 (with a maximum value of 5 Oe) was found to occur only at 2 K and at 10 K at particular field-cooling values. At 2 K, the exchange bias was observed only at the smallest field-cooled values of 0.5 T, and 1 T, whereas at 10 K, the exchange bias was observed only at 0.5 T. Additionally, an unconventional exchange bias in sample S2 (with a maximum value of 20 Oe) was found to occur at all temperatures and all field-cooling values. The exchange bias effect appears after field-cooling from room temperature (300 K), which is much lower than both the $T_C$ of the shell (which is above 820 K) and the $T_C$ of the core (which is around 850 K).

Figure 2B:
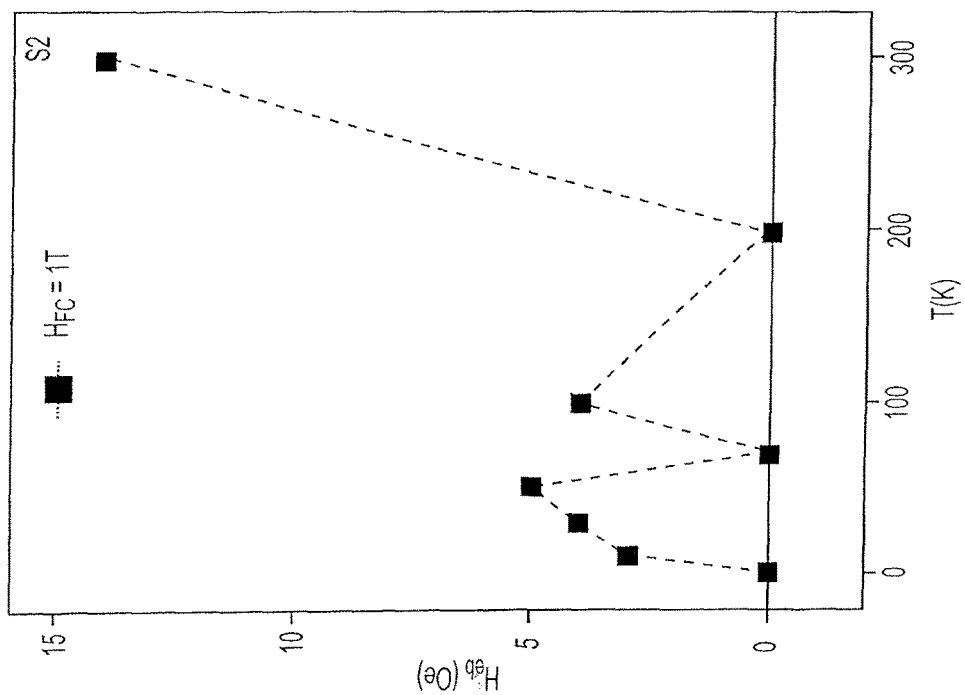
FIG. 2B is a plot of exchange bias field as a function of temperature for the second sample at a field-cooling value of 1.0 T.
Figure 2A:
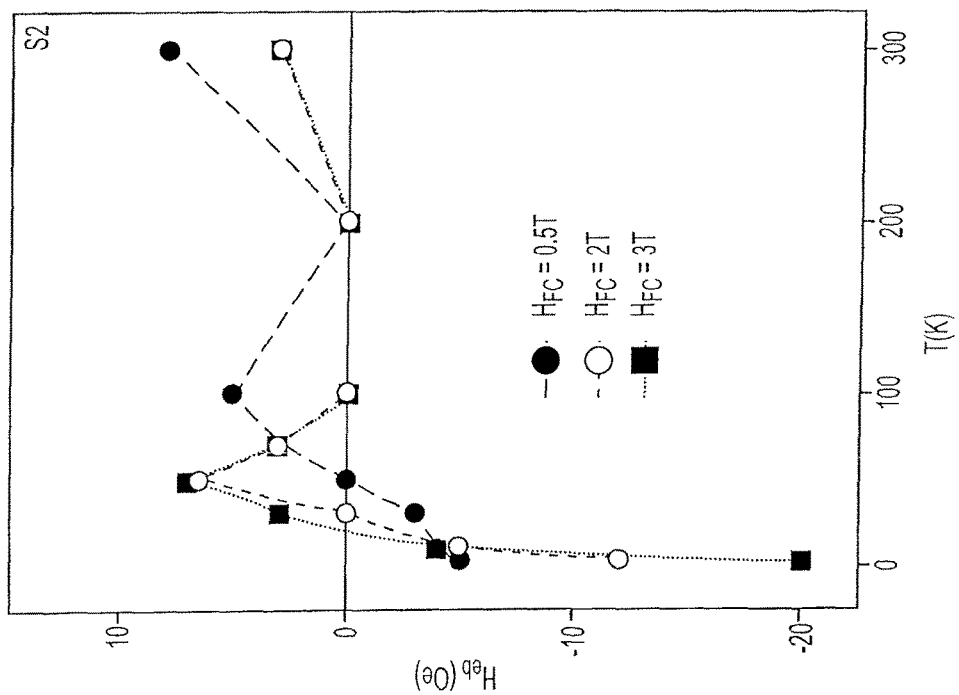
FIG. 2A is a plot of exchange bias field as a function of temperature for the second sample at field-cooling values of 0.5 T, 2.0 T and 3.0 T.
Figure 3A:
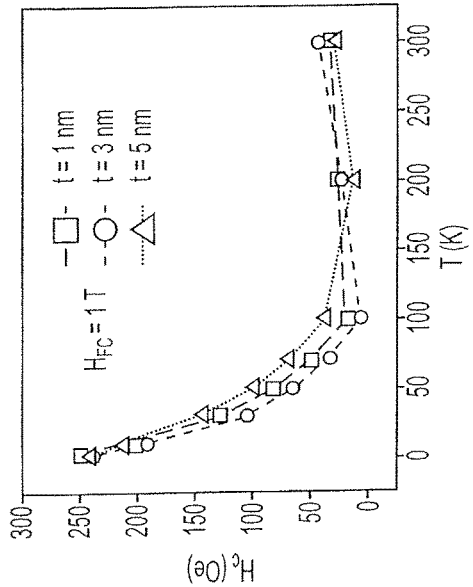
FIG. 3A is a plot of coercivity ($H_C$, in oersteds) as a function of temperature after field cooling for the three samples having a shell thickness of 1 nm, 3 nm, and 5 nm, respectively, and with a field-cooling value of 0.5 T.
Figure 3B:
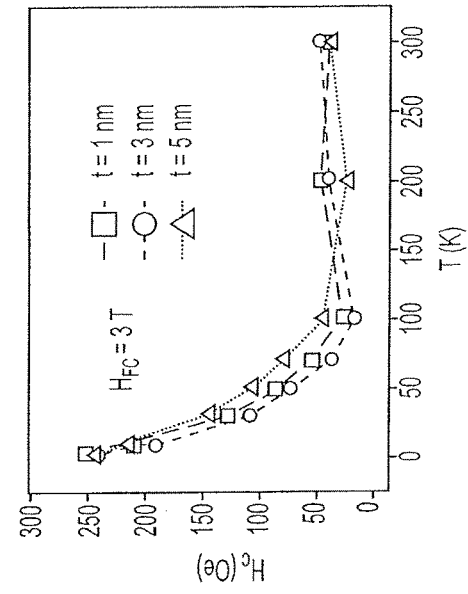
FIG. 3B is a plot of coercivity ($H_C$, in oersteds) as a function of temperature after field cooling for the three samples having a shell thickness of 1 nm, 3 nm, and 5 nm, respectively, and with a field-cooling value of 1.0 T.
Figure 3C:
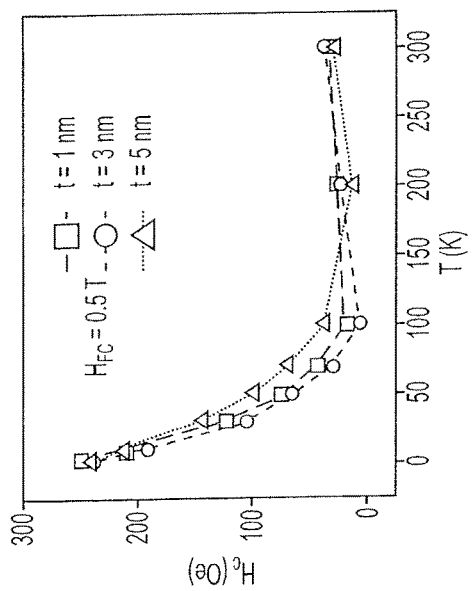
FIG. 3C is a plot of coercivity ($H_C$, in oersteds) as a function of temperature after field cooling for the three samples having a shell thickness of 1 nm, 3 nm, and 5 nm, respectively, and with a field-cooling value of 2.0 T.
Figure 3D:
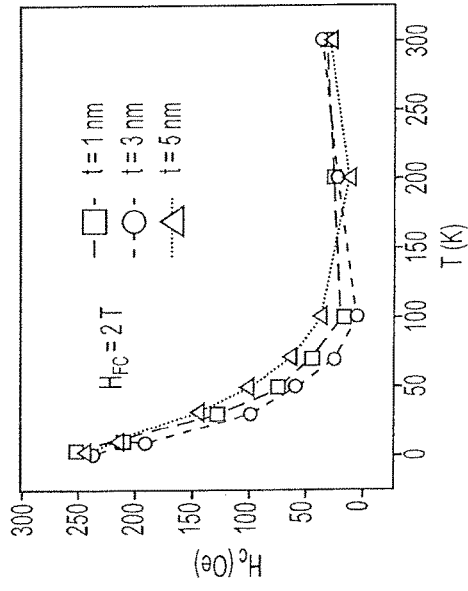
FIG. 3D is a plot of coercivity ($H_C$, in oersteds) as a function of temperature after field cooling for the three samples having a shell thickness of 1 nm, 3 nm, and 5 nm, respectively, and with a field-cooling value of 3.0 T.

Further, the exchange bias in sample S2 has a non-monotonic behavior with temperature, as well as with field-cooling. This is opposite of the familiar exchange bias behavior in other systems, where exchange bias decreases with temperature and increases with the increase of the field-cooling value. The exchange bias in sample S2 did not vanish at 300 K at all field-cooled values. Additionally, negative as well as positive exchange bias was observed in sample S2. The switch from negative to positive exchange bias in this sample occurred at temperatures of 50 K, 30 K and 21 K, for field-cooling values of 0.5 T, 2 T and 3 T, respectively. Thus, in this FIM/FIM core/shell structure, a shell thickness of 3 nm represents a critical thickness at which exchange bias occurs at nearly all temperatures and at all field-cooling values. FIG. 2A is a plot of exchange bias field, $H_{eb}$, as a function of temperature, T, for the second sample, S2, at field-cooling values of 0.5 T, 2.0 T and 3.0 T. FIG. 2B is a plot of exchange bias field, $H_{eb}$, as a function of temperature, T, for the second sample at a field-cooling values of 1.0 T.

In the zero-field-cooled state (at a particular temperature), the shell thickness has a noticeable role on coercivity, where it was found to increase at some temperature values and decrease at others. In the field-cooled state (at particular field-cooling values and temperatures), shell thickness does not have any noticeable effect on coercivity. As a function of temperature, coercivity in all samples (at zero-field-cooling and at all field-cooling values) was observed to initially decrease monotonically and sharply with increasing temperature, reaching a non-zero minimum value at 100 K for samples S1 and S2, and at 200 K for sample S3. As the temperature increases above 100 K (for samples S1 and S2) and above 200 K for sample S3, a slow and almost linear increase of coercivity with temperature takes place and continues up to 300 K. The increase of coercivity with temperature after reaching a minimum value and the non-vanishing of coercivity at room temperature in all samples (at zero-field-cooling and at all field-cooled values) is a particularly significant observation in this FIM/FIM core/shell structure. This behavior of coercivity is opposite of that in other systems, where coercivity keeps decreasing with temperature. After field-cooling at 0.5 T, the magnitudes of coercivity decreased in all samples at all temperatures. No significant additional changes in the magnitudes of coercivity occurred at higher field-cooling values in all samples. Thus, 0.5 T is considered to be a critical field-cooling value at which coercivity starts decreasing in all samples at all temperatures.

Thus, for this FIM/FIM core/shell structure, there are two critical parameters affecting coercivity. The first critical parameter is a field-cooling value of 0.5 T, which represents a critical value at which five significant observations occur in coercivity. These are: (1) the magnitude of coercivity decreases in all samples at all temperatures (except at 2 K in sample S1); (2) a dip occurs in the coercivity in sample S2, both in the zero-field-cooling and field-cooling states; (3) the rate of decrease of coercivity with temperature becomes the same in all samples at temperatures below the temperature of the minimum coercivity (100 K for samples S1 and S2, and above 200 K for sample S3); (4) the rate of increase of coercivity with temperature becomes the same in all samples above the temperature of the minimum coercivity; and (5) the magnitudes of coercivity at temperature above the temperature of the minimum coercivity become nearly the same in all samples. The second critical parameter is the 3.0 nm shell thickness at which the coercivity displays a dip in both the zero-field-cooling and field-cooling states nearly at all temperatures.

Figure 4A:
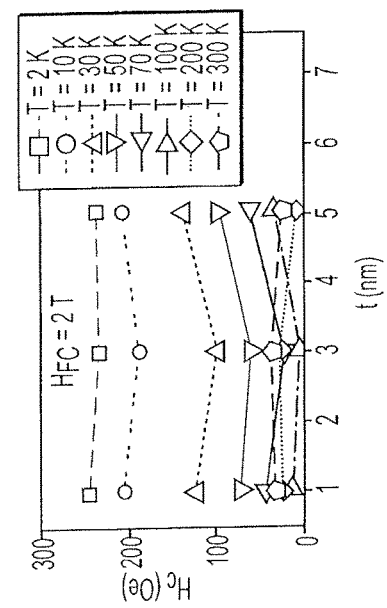
FIG. 4A is a plot of coercivity as a function of shell thickness for samples of $Fe_3O_4/\gamma\text{-}Fe_2O_3$ core/shell nanoparticles produced by the present method for zero-field-cooling (ZFC) at temperatures of 2 K, 10 K, 30 K, 50 K, 70 K, 100 K, 200 K and 300 K.
Figure 4B:
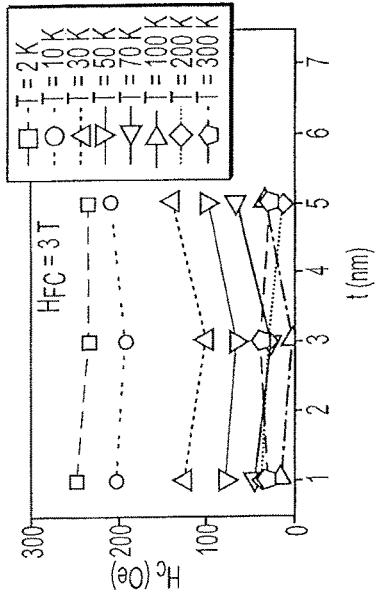
FIG. 4B is a plot of coercivity as a function of shell thickness for samples of $Fe_3O_4/\gamma$-$Fe_2O_3$ core/shell nanoparticles produced by the present method for a field-cooling value of 0.5 T at temperatures of 2 K, 10 K, 30 K, 50 K, 70 K, 100 K, 200 K and 300 K.
Figure 4C:
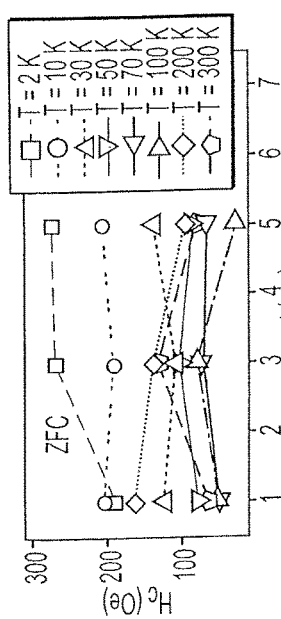
FIG. 4C is a plot of coercivity as a function of shell thickness for samples of $Fe_3O_4/\gamma$-$Fe_2O_3$ core/shell nanoparticles produced by the present method for a field-cooling value of 1.0 T at temperatures of 2 K, 10 K, 30 K, 50 K, 70 K, 100 K, 200 K and 300 K.
Figure 4D:
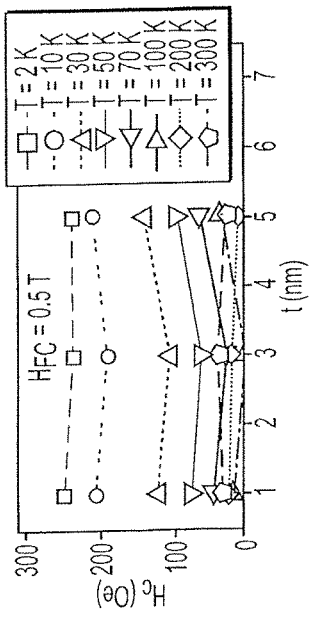
FIG. 4D is a plot of coercivity as a function of shell thickness for samples of $Fe_3O_4/\gamma$-$Fe_2O_3$ core/shell nanoparticles produced by the present method for a field-cooling value of 2.0 T at temperatures of 2 K, 10 K, 30 K, 50 K, 70 K, 100 K, 200 K and 300 K.
Figure 4E:
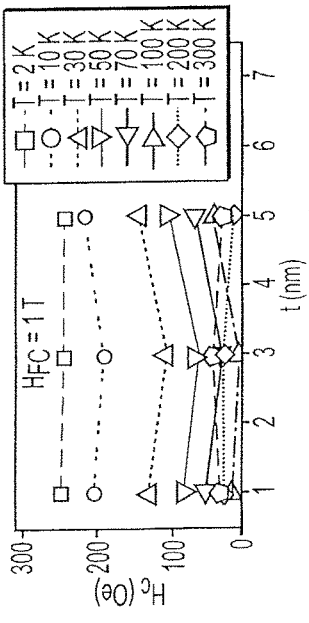
FIG. 4E is a plot of coercivity as a function of shell thickness for samples of $Fe_3O_4/\gamma$-$Fe_2O_3$ core/shell nanoparticles produced by the present method for a field-cooling value of 3.0 T at temperatures of 2 K, 10 K, 30 K, 50 K, 70 K, 100 K, 200 K and 300 K.

FIGS. 3A, 3B, 3C and 3D are plots comparing coercivity, $H_c$, as a function of temperature, T, after field-cooling for the first sample, S1, which has a shell thickness of 1 nm, for the second sample, S2, which has a shell thickness of 3 nm, and for the third sample, S3, which has a shell thickness of 5 nm, with a field-cooling value of 0.5 T, 1.0 T, 2.0 T and 3.0 T, respectively. FIG. 4A is a plot comparing coercivity, $H_c$, as a function of shell thickness, t, for samples of $Fe_3O_4$/$\gamma$-$Fe_2O_3$ core/shell nanoparticles produced by the present method, for zero-field-cooling (ZFC), at temperatures of 2 K, 10 K, 30 K, 50 K, 70 K, 100 K, 200 K and 300 K.

Similarly, FIGS. 4B, 4C, 4D and 4E are plots comparing coercivity as a function of shell thickness for samples of $Fe_3O_4/\gamma$-$Fe_2O_3$ core/shell nanoparticles produced by the present method, at temperatures of 2 K, 10 K, 30 K, 50 K, 70 K, 100 K, 200 K and 300 K, for field-cooling values, $H_{FC}$, of 0.5 T, 1.0 T, 2.0 T and 3.0 T, respectively.

Shell thickness-dependent saturation magnetization values were found to remain nearly the same with increases of the temperature from 2 K to 100 K. A noticeable decrease in the shell thickness-dependent saturation magnetization values appeared above 100 K. At 200 K, saturation magnetization values were found to be 73 emu/g, 77 emu/g and 80 emu/g in samples S1, S2 and S3, respectively. This reflects only a decrease of less than 5% of the initial values. A pronounced decrease in the shell thickness-dependent saturation magnetization values occurred at 300 K, with minimum values of 66 emu/g, 69 emu/g and 72 emu/g in samples S1, S2 and S3, respectively. This reflects only a decrease of nearly 14% of the initial values. Thus, in the zero-field-cooled state, the maximum value of saturation magnetization obtained is 84 emu/g in sample S3.

After field-cooling at 0.5 T, the magnitudes of saturation magnetization at 2 K changed only slightly in samples S1 and S3 (where the saturation magnetization increased from 77 emu/g to 80 emu/g in sample S1 and decreased slightly from 84 emu/g to 80 emu/g in sample S3). After field-cooling at 0.5 T, the saturation magnetization at 2 K in sample S2 displays a drastic increase, reaching 120 emu/g. This indicates an increase of exactly 50% of its value in the ZFC state and nearly 50% increase of its bulk value. This reflects the significant role of field-cooling at 0.5 T with regard to enhancing the saturation magnetization in sample S2.

After field-cooling, the magnitudes of saturation magnetization at temperatures up to 100 K remained almost equal to those at 2 K in all samples. However, a noticeable decrease of the saturation magnetization values occurs at 200 K and 300 K in all samples. This clearly reflects the role of field-cooling at 0.5 T in enhancing the saturation magnetization in sample S2, even at room temperature. Larger field-cooling values displayed similar effects as that of the 0.5 T field-cooling value. Thus, the 0.5 T can be considered as a critical field-cooling value in sample S2, where a drastic increase in saturation magnetization occurs. This also indicates that the shell thickness of 3 nm is a critical thickness in this core/shell nanoparticle system, where a very large enhancement in saturation magnetization occurs at the field-cooling value of 0.5 T at all temperatures, with a value of 120 emu/g at temperatures up to 100 K, and with only a slight decrease at temperatures above 100 K.

Figure 5A:
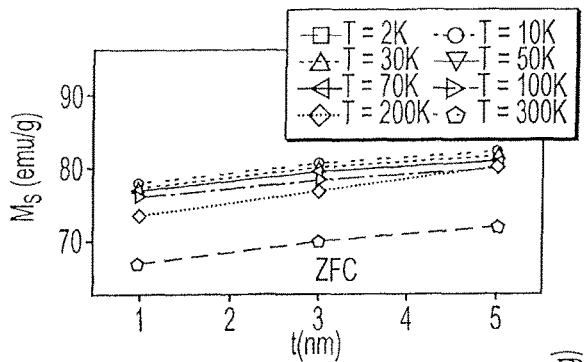
FIG. 5A is a plot of saturation magnetization as a function of shell thickness for samples of $Fe_3O_4/\gamma$-$Fe_2O_3$ core/shell nanoparticles produced by the present method for zero-field-cooling (ZFC) at temperatures of 2 K, 10 K, 30 K, 50 K, 70 K, 100 K, 200 K and 300 K.
Figure 5B:
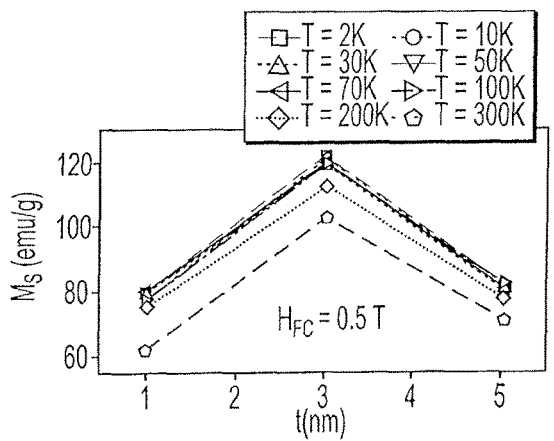
FIG. 5B is a plot of saturation magnetization as a function of shell thickness for samples of $Fe_3O_4/\gamma$-$Fe_2O_3$ core/shell nanoparticles produced by the present method for a field-cooling value of 0.5 T at temperatures of 2 K, 10 K, 30 K, 50 K, 70 K, 100 K, 200 K and 300 K.
Figure 5C:
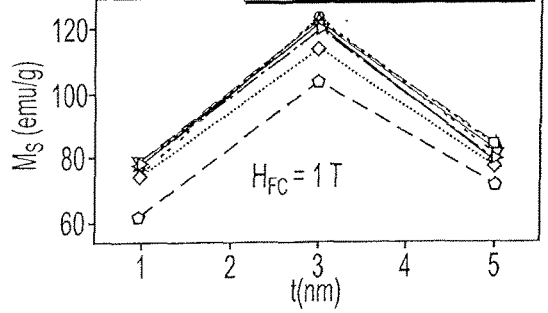
FIG. 5C is a plot of saturation magnetization as a function of shell thickness for samples of $Fe_3O_4/\gamma$-$Fe_2O_3$ core/shell nanoparticles produced by the present method for a field-cooling value of 1.0 T, at temperatures of 2 K, 10 K, 30 K, 50 K, 70 K, 100 K, 200 K and 300 K.
Figure 5D:
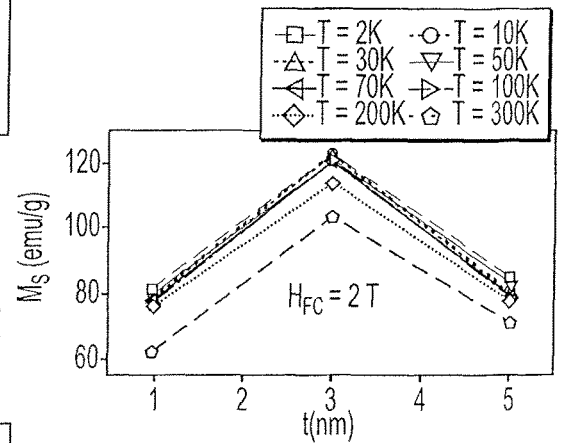
FIG. 5D is a plot of saturation magnetization as a function of shell thickness for samples of $Fe_3O_4/\gamma$-$Fe_2O_3$ core/shell nanoparticles produced by the present method for a field-cooling value of 2.0 T at temperatures of 2 K, 10 K, 30 K, 50 K, 70 K, 100 K, 200 K and 300 K.
Figure 5E:
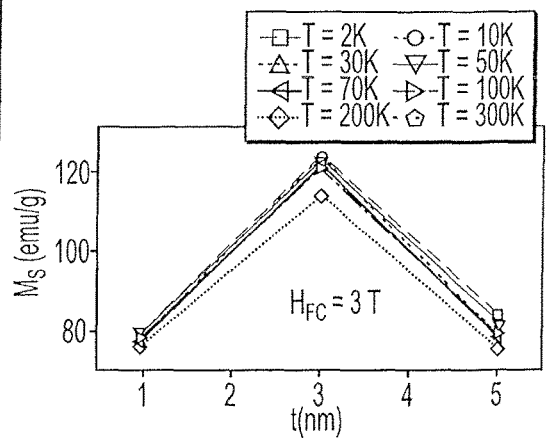
FIG. 5E is a plot of saturation magnetization as a function of shell thickness for samples of $Fe_3O_4/\gamma$-$Fe_2O_3$ core/shell nanoparticles produced by the present method for a field-cooling value of 3.0 T at temperatures of 2 K, 10 K, 30 K, 50 K, 70 K, 100 K, 200 K and 300 K.

FIG. 5A is a plot comparing saturation magnetization, $M_S$, as a function of shell thickness, t, for samples of $Fe_3O_4/\gamma$-$Fe_2O_3$ core/shell nanoparticles produced by the present method of making iron oxide nanoparticles, for zero-field-cooling (ZFC) at temperatures of 2 K, 10 K, 30 K, 50 K, 70 K, 100 K, 200 K and 300 K. Similarly, FIGS. 5B, 5C, 5D and 5E are plots comparing saturation magnetization, $M_S$, as a function of shell thickness, t, for samples of $Fe_3O_4/\gamma$-$Fe_2O_3$ core/shell nanoparticles produced by the present method at temperatures of 2 K, 10 K, 30 K, 50 K, 70 K, 100 K, 200 K and 300 K, for field-cooling values, $H_{FC}$, of 0.5 T, 1.0 T, 2.0 T and 3.0 T, respectively.

The $Fe_3O_4/\gamma$-$Fe_2O_3$ core/shell nanoparticles produced by the present method have potential applications in medicine as well as data storage. Magnetic hyperthermia is the field of treating cancer by supplying heat to tumor cells using magnetic nanoparticles (MNPs) and an alternating magnetic field. This method shows promise for treatment of small or deep-seated tumors. This method is based on the observation that tumor cells can be destroyed by heating the cells to a temperature between 43° C. and 46° C., while healthy cells are less affected. The heating process is enabled by the application of an alternating magnetic field of suitable amplitude and frequency. One of the major issues in the application of magnetic hyperthermia is the reduction of the amount of MNPs that can be used in living organs. In order to achieve this goal, the power dissipation or heating efficiency of MNPs should be enhanced. The specific loss power (SLP), which is a measure of the heating efficiency of nanoparticles, depends on intrinsic magnetic properties of the material, along with size, composition and the frequency and intensity of the applied magnetic field. The intrinsic material parameters, such as magnetic anisotropy and saturation magnetization, play the major role in controlling the heating efficiency of nanoparticles. The combination of two phases in a core/shell structure produces magnetic anisotropy and saturation magnetization values that are different than those of the single phase core or shell materials. Thus, the heating efficiency of these core/shell nanoparticles can be tuned to enhance their heating efficiency.

It has been found that the specific loss power of core/shell nanoparticles is better than that of both conventional materials and single phase nanoparticles of similar sizes. In particular, inverse $MnFe_2O_4/CoFe_2O_4$ nanoparticles have been shown to have outstanding hyperthermia properties. Compared to single phase iron oxide nanoparticles, the core-shell of iron-iron oxides nanocomposites have been reported to have much better heating in an alternating magnetic field and, thus, have been suggested as good candidates for both hyperthermia and magnetic resonance imaging applications. Further, $Fe_3O_4/\gamma$-$Fe_2O_3$ core-shell magnetic nanoparticles have been shown to have superior heating efficiency. A corresponding significant role of magnetic anisotropies and shell-thickness on the efficiency of magnetic induction heating was also found. The magnetic interfacial coupling of these $Fe_3O_4/\gamma$-$Fe_2O_3$ core-shell MNPs have been reported to strongly promote magnetically induced heat generation. The role of the core-shell interface on exchange bias and coercivity has been investigated in monodisperse $Fe_3O_4/\gamma$-$Fe_2O_3$ core/shell nanoparticles with a very narrow size distribution, with diameters of 2-30 nm. In this study, the $Fe_3O_4$ core dimensions were varied while the $\gamma$-$Fe_2O_3$ shell thickness remained fixed.

Magnetic nanoparticles present several advantages when compared to conventional materials for certain magnetic resonance imaging (MRI) applications. Superparamagnetic iron oxide nanoparticles are known to decrease the transverse relaxation time ($T_2$) of water protons when they are influenced by the nanoparticle dipole moment. This $T_2$ decrease leads to an increase of the negative contrast. The relaxivity (the inverse of the relaxation time $R_2=1/T_2$) is proportional to the magnetic moment. Thus, enhancing the magnetic moment of the magnetic nanoparticles is an efficient way to improve $T_2$-weighted imaging. However, the correlation between $R_2$ and saturation magnetization of nanoparticles is not will established and depends on other parameters. Thus, controlling such parameters may influence the efficiency of magnetic nanoparticles for MRI. In this regard, there is an increasing interest in the study of different types of bi-magnetic core/shell nanoparticles for MRI.

Due to their enhanced magnetic properties, iron/iron oxide core/shell nanoparticles were found to have a much stronger $T_2$ shortening effect than that of single phase iron-oxide nanoparticles with the same core size. Compared with iron oxide nanoparticles, iron/iron oxides core/shell nanoparticles showed a strong increase of the $R_1$ values at low applied magnetic fields and a strong increase of the $R_2$ measured at high applied magnetic fields. Thus, this core/shell structure suspension can be used both as $T_1$ and $T_2$ contrast agents. Core/shell magnetic nanoparticles of $CoFe_2O_4/ZnFe_2O_4$ and $CoFe_2O_4/MnFe_2O_4$ have been found to be excellent $T_2$ contrast agents. Core/shell/shell structured $Fe_3O_4/SiO_2/Gd_2O(CO_3)_2$ nanoparticles were reported to be a good $T_1$ and $T_2$ dual model contrast agent for magnetic resonance imaging. The introduction of the separating $SiO_2$ layer was found to modulate the magnetic coupling between $Gd_2O(CO_3)_2$ and $Fe_3O_4$ by changing the thickness of the $SiO_2$ layer, leading to appropriate $T_1$ and $T_2$ signals.

With regard to data storage, increasing the areal density requires downscaling of the magnetic materials and other components of the data storage system (i.e., the read head, the write head and the media). Thus, magnetic nanoparticles are promising candidates for the next generation of magnetic data storage. However, it is well known now that there is a limit on the size of magnetic nanoparticles, below which thermal stability becomes a major problem and the superparamagnetic state is reached. In the superparamagnetic state, a MNP behaves as a paramagnetic atom with a giant spin. At temperatures below the blocking temperature, the thermal agitation becomes small and will not be able to cause fluctuations in the orientations of the magnetic moments of the nanoparticles, where they freeze in random orientations.

Technological applications of MNPs demand their thermal stability. If thermal energy ($k_BT$, where $k_B$ is Boltzmann's constant) exceeds the magnetic anisotropy energy (magnetic energy barrier) between stable magnetic directions, the nanoparticle (NP) relaxes from the blocked state to the superparamagnetic state, where the magnetic moment of the NP starts flipping randomly and will not be fixed in a specific direction.

The stability of the magnetic media for data storage is primarily determined by the anisotropy energy, which is the amount of energy required to reverse the magnetization from one stable state to the other. This anisotropy energy depends on several factors, most importantly the effective magnetic anisotropy constant, which is correlated with the coercivity. In terms of magnetic stability, the more energy that is required to randomize the magnetic moments (spins) of the magnetic material, either thermally or via an applied field, the less likely that the information stored in the material will be erased due to excess heat or stray magnetic fields. Thus, attempts to find stable magnetic storage materials depend on the tailoring of the effective magnetic anisotropy of the materials. The effective anisotropy depends on several factors, such as size and structure of the magnetic material. The material can be structured of two different magnetic phases, where exchange bias across the interface is expected to provide larger effective anisotropy and coercivity than those of the isolated phases. Core-shell nanoparticles are typical nanostructures where the effective anisotropy and coercivity can be controlled by controlling the interface exchange cooping. Magnetic nanostructures are the main contributor in the current magnetic hard disk drive technology.

It is to be understood that the method of synthesizing magnetite/maghemite core/shell nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing magnetite/maghemite ($Fe_3O_4/\gamma\text{-}Fe_2O_3$) core/shell nanoparticles, comprising the steps of:
   mixing an aqueous solution of a ferric salt with an aqueous solution of a ferrous salt;
   adding ammonium hydroxide solution to the mixture until the pH of the mixture is 10;
   maintaining the mixture at a temperature of 80° C. exposed to atmospheric oxygen at atmospheric pressure for between one hour and three hours to form a precipitate; and
   drying the precipitate to yield $Fe_3O_4/\gamma\text{-}Fe_2O_3$ core/shell nanoparticles.

2. The method of synthesizing magnetite/maghemite ($Fe_3O_4/\gamma\text{-}Fe_2O_3$) core/shell nanoparticles as recited in claim 1, wherein the step of mixing the aqueous solutions comprises mixing an aqueous solution of $FeCl_3.6H_2O$ and an aqueous solution of $FeCl_3.6H_2O$ at room temperature.

3. The method of synthesizing magnetite/maghemite ($Fe_3O_4/\gamma\text{-}Fe_2O_3$) core/shell nanoparticles as recited in claim 1, wherein the step of adding the ammonium hydroxide solution comprises adding the ammonium hydroxide solution in dropwise manner until the mixture has a pH of 10.

4. The method of synthesizing magnetite/maghemite ($Fe_3O_4/\gamma\text{-}Fe_2O_3$) core/shell nanoparticles as recited in claim 1, wherein the step of drying the precipitate comprises drying the precipitate at a temperature of 120° C. under vacuum.

5. The method of synthesizing magnetite/maghemite ($Fe_3O_4/\gamma\text{-}Fe_2O_3$) core/shell nanoparticles as recited in claim 1, wherein the step of maintaining the mixture at a temperature of 80° C. comprises maintaining the mixture at a temperature of 80° C. for one hour, whereby the nanoparticles have a shell thickness of 1 nm.

6. The method of synthesizing magnetite/maghemite ($Fe_3O_4/\gamma\text{-}Fe_2O_3$) core/shell nanoparticles as recited in claim 1, wherein the step of maintaining the mixture at a temperature of 80° C. comprises maintaining the mixture at a temperature of 80° C. for two hours, whereby the nanoparticles have a shell thickness of 3 nm.

7. The method of synthesizing magnetite/maghemite ($Fe_3O_4/\gamma\text{-}Fe_2O_3$) core/shell nanoparticles as recited in claim 1, wherein the step of maintaining the mixture at a temperature of 80° C. comprises maintaining the mixture at a temperature of 80° C. for three hours, whereby the nanoparticles have a thickness of 5 nm.

8. A method of making iron oxide nanoparticles, comprising the steps of:
   mixing an aqueous solution of $FeCl_3.6H_2O$ and an aqueous solution of $FeCl_2.4H_2O$ to form a first solution;
   adding ammonium hydroxide solution to the first solution to form a second solution;
   maintaining the second solution at a temperature of approximately 80° C. for a selected reaction time to form a precipitate, wherein the selected reaction time is between approximately one hour and approximately three hours, and wherein the selected reaction time is selected based upon a desired nanoparticle shell thickness, wherein the shell thickness is between 1 nm and 5 nm; and
   drying the precipitate to yield iron oxide ($Fe_3O_4/\gamma\text{-}Fe_2O_3$) nanoparticles, wherein the step of drying comprises drying the precipitate at a temperature of approximately 120° C. under vacuum to obtain a fixed core diameter of 8 nm.

* * * * *